US010973983B2

(12) United States Patent
Prager

(10) Patent No.: US 10,973,983 B2
(45) Date of Patent: Apr. 13, 2021

(54) DRUG DELIVERY DEVICE WITH AT LEAST ONE TRANSPARENT REGION OF HOUSING

(71) Applicant: SANOFI-AVENTIS DEUTSCHLAND GMBH, Frankfurt am Main (DE)

(72) Inventor: Roman Prager, Gänserndorf (AT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 519 days.

(21) Appl. No.: 15/517,243

(22) PCT Filed: Oct. 5, 2015

(86) PCT No.: PCT/EP2015/072904
§ 371 (c)(1),
(2) Date: Apr. 6, 2017

(87) PCT Pub. No.: WO2016/055400
PCT Pub. Date: Apr. 14, 2016

(65) Prior Publication Data
US 2017/0304552 A1 Oct. 26, 2017

(30) Foreign Application Priority Data
Oct. 6, 2014 (EP) .................................... 14187694

(51) Int. Cl.
A61M 5/315 (2006.01)
A61M 5/31 (2006.01)
A61M 5/14 (2006.01)
(52) U.S. Cl.
CPC ...... A61M 5/31568 (2013.01); A61M 5/3146 (2013.01); A61M 5/3155 (2013.01);
(Continued)

(58) Field of Classification Search
CPC ............ A61M 5/3155; A61M 5/31525; A61M 5/31555; A61M 5/31568;
(Continued)

(56) References Cited

U.S. PATENT DOCUMENTS 3,566,602 A * 3/1971 Bergey .................... G04G 9/128
368/79
3,575,129 A * 4/1971 Sullivan ................... G01P 3/36
116/57
(Continued)

FOREIGN PATENT DOCUMENTS

DE 102004063652 7/2006
WO WO 2009/070911 6/2009
(Continued)

OTHER PUBLICATIONS

Woodford, Chris. Mirrors—the science of reflection. Available online at https://web.archive.org/web/20131002201129/https://www.explainthatstuff.com/howmirrorswork.html (accessed Mar. 25, 2019) (published 2013) (Year: 2013).*
(Continued)

Primary Examiner — William R Carpenter
Assistant Examiner — Larry R. Wilson
(74) Attorney, Agent, or Firm — Fish & Richardson P.C.

(57) ABSTRACT

The present disclosure relates to a drug delivery device comprising: a housing; a moveable number sleeve disposed within the housing and having numbers printed thereon; and a transparent window occupying an aperture of the housing and covering the number sleeve such that the number sleeve is visible through the transparent window. At least one region of the housing located adjacent to the transparent window is transparent to visible light and is in optical communication with the transparent window.

13 Claims, 5 Drawing Sheets

(52) U.S. Cl.
CPC ...... *A61M 5/3158* (2013.01); *A61M 5/31535* (2013.01); *A61M 5/14* (2013.01); *A61M 5/31551* (2013.01); *A61M 2005/3126* (2013.01); *A61M 2205/3306* (2013.01); *A61M 2205/3375* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/587* (2013.01); *A61M 2205/6072* (2013.01); *A61M 2205/6081* (2013.01); *A61M 2205/8206* (2013.01)

(58) Field of Classification Search
CPC .. A61M 2005/3125; A61M 2005/3126; A61M 5/002; A61M 5/14; A61M 5/20; A61M 5/24; A61M 5/31; A61M 5/3146; A61M 5/31533; A61M 5/31535; A61M 5/31551; A61M 5/3158; A61M 2205/3569; A61M 2205/3592; A61M 2205/50; A61M 2205/502; A61M 2205/52; A61M 2205/58; A61M 2205/581; A61M 2205/583; A61M 2205/584; A61M 2205/587; A61M 2205/6063; A61M 2205/6072; A61M 2205/6081; A61B 5/0017; A61B 5/1455; A61B 5/14532; A61B 5/4839; A61B 7/04; G02B 6/00; G02B 6/0001; G06F 19/3468; H04B 10/00; F21Y 2103/33; F21Y 2115/10; G09F 13/02; G09F 2013/222
See application file for complete search history.

(56) References Cited

U.S. PATENT DOCUMENTS

| | | | | |
|---|---|---|---|---|
| 3,966,303 | A * | 6/1976 | Yamamoto | G02B 6/0008 349/62 |
| 5,739,876 | A * | 4/1998 | Stewart | G02F 1/1336 349/1 |
| 9,155,842 | B2 * | 10/2015 | Matthias | A61M 5/31525 |
| 2004/0136174 | A1 * | 7/2004 | Yu | G02B 6/0043 362/619 |
| 2008/0157009 | A1 * | 7/2008 | Wittenberg | G02F 1/133602 250/494.1 |
| 2011/0149603 | A1 * | 6/2011 | Tortora | G02B 6/002 362/612 |
| 2011/0276006 | A1 * | 11/2011 | Matthias | A61M 5/31525 604/189 |
| 2012/0165748 | A1 * | 6/2012 | Plumptre | A61M 5/31551 604/207 |
| 2013/0197445 | A1 * | 8/2013 | Schabbach | A61M 5/31533 604/189 |
| 2014/0380218 | A1 * | 12/2014 | Johnnie | A61B 5/150358 715/771 |

FOREIGN PATENT DOCUMENTS

| | | | | |
|---|---|---|---|---|
| WO | WO 2010/003569 | | 1/2010 | |
| WO | WO-2010003569 A1 * | | 1/2010 | ........ A61M 5/31525 |
| WO | WO 2013/004843 | | 1/2013 | |
| WO | WO 2013/120776 | | 8/2013 | |
| WO | WO-2013120776 A1 * | | 8/2013 | ........ A61M 5/31525 |
| WO | WO 2014/139915 | | 9/2014 | |

OTHER PUBLICATIONS

International Preliminary Report on Patentability in International Application No. PCT/EP2015/072904, dated Apr. 11, 2017, 10 pages.
International Search Report and Written Opinion in International Application No. PCT/EP2015/072904, dated Dec. 7, 2015, 14 pages.

* cited by examiner

DRUG DELIVERY DEVICE WITH AT LEAST ONE TRANSPARENT REGION OF HOUSING

CROSS-REFERENCE TO RELATED APPLICATIONS

This application is a U.S. national stage application under 35 USC § 371 of International Application No. PCT/EP2015/072904, filed on Oct. 5, 2015, which claims priority to European Patent Application No. 14187694.6 filed on Oct. 6, 2014, the entire contents of which are incorporated herein by reference.

TECHNICAL FIELD

The present disclosure relates to a drug delivery device comprising a number sleeve within a housing, a transparent window covering the number sleeve and at least one transparent region of housing located adjacent the transparent window. The present disclosure also relates to a supplementary device for attachment to this drug delivery device and to a system comprising both the drug delivery device and supplementary device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, for instance information on the injected insulin type and dose.

SUMMARY

A first aspect provides a drug delivery device comprising a housing; a moveable number sleeve disposed within the housing and having numbers printed thereon; and a transparent window occupying an aperture of the housing and covering the number sleeve such that the number sleeve is visible through the transparent window, wherein at least one region of the housing located adjacent the transparent window is transparent to visible light and is in optical communication with the transparent window.

The at least one region of the housing located adjacent the transparent window may comprise a material which is transparent to visible light and is configured to guide input light towards the transparent window so as to illuminate the number sleeve.

The at least one region of the housing located adjacent the transparent window may comprise one or more light guides configured to output light into the transparent window. One or more internal surfaces of the light guide may be reflective.

The at least one region of the housing located adjacent the transparent window may comprise a continuous extension of the transparent window. One or more internal surfaces of the continuous extension of the transparent window may be reflective.

The housing may comprise two regions of transparent material located adjacent opposite sides of the transparent window.

Each of the at least one regions of the housing located adjacent the transparent window may comprise a recess or an aperture in the housing.

A second aspect provides a supplementary device for attachment to an injection device, the supplementary device comprising an imaging arrangement configured to capture an image of a moveable number sleeve of the injection device, the number sleeve disposed beneath a transparent window; and one or more illumination sources configured to illuminate the number sleeve indirectly by being positioned such that when the supplementary device is attached to the injection device light from the one or more illumination sources is incident on a region of the housing located adjacent the transparent window, the region being in optical communication with the transparent window.

The one or more illumination sources may be positioned such that light emitted from the one or more light sources is not directly incident on the transparent window.

A third aspect provides a system comprising the drug delivery device of the first aspect and the supplementary device of the second aspect.

Embodiments will now be described, by way of example only, with reference to the accompanying drawings.

BRIEF DESCRIPTION OF THE FIGURES

The figures show:

FIG. 1b shows a perspective view of some detail of the drug delivery device of FIG. 1a;

DETAILED DESCRIPTION OF THE FIGURES

In the following, embodiments will be described with reference to an insulin injection device. The present invention is however not limited to such application and may equally well be deployed with injection devices that eject other medicaments, or with other types of medical devices.

Figure 1A:
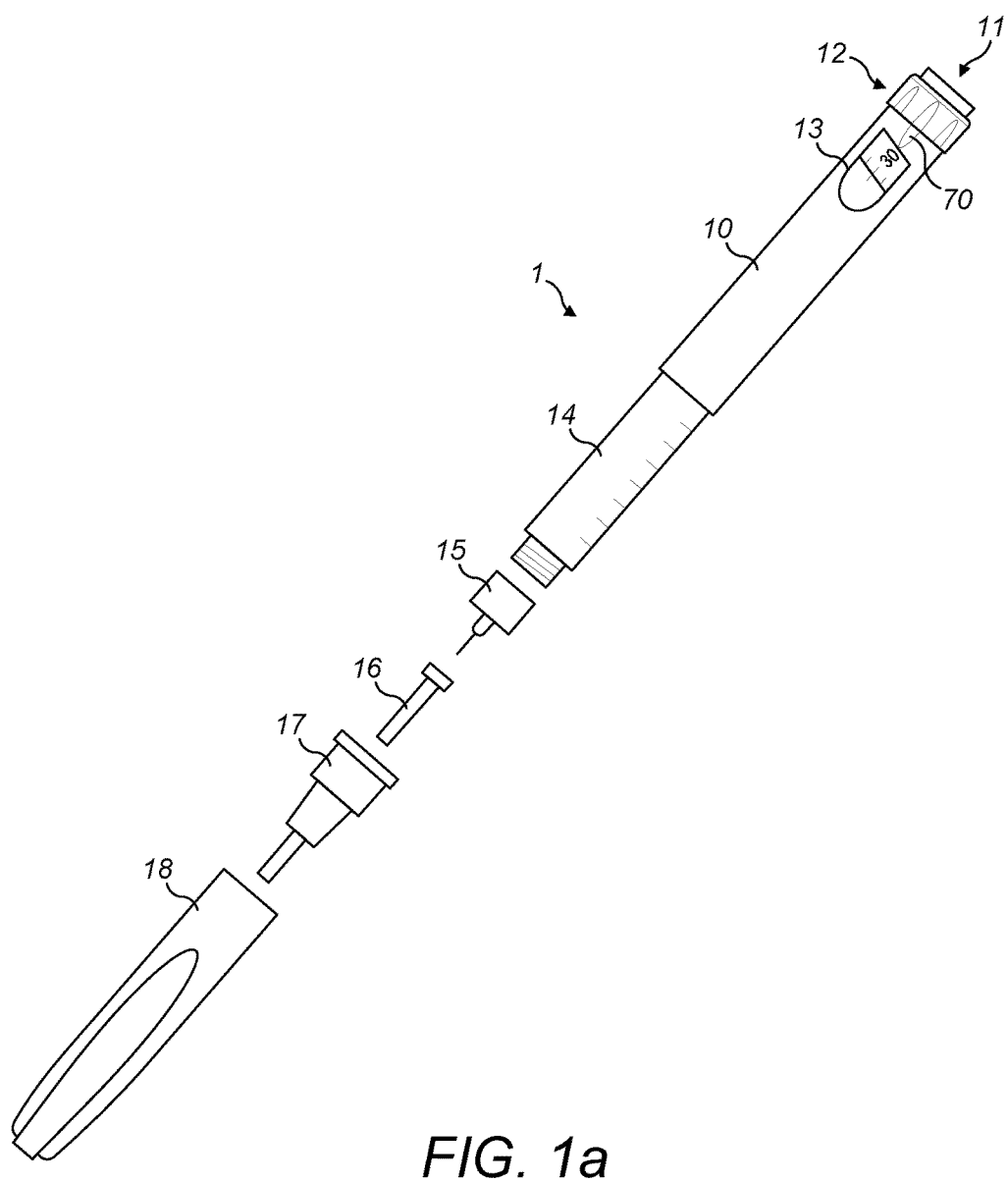
FIG. 1a: an exploded view of an drug delivery device.

FIG. 1 is an exploded view of an injection device 1 (also referred to herein as a drug delivery device 1, injection pen 1 or pen device 1), which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently. A label (not shown) is provided on the housing 10. The label includes information about the medicament included within the injection device, including information identifying the medicament. The information identifying the medicament may be in the form of text. The information identifying the medicament may also be in the form of a color. The information identifying the medicament may also be encoded into a barcode, QR code or the like. The information identifying the medicament may also be in the form of a black and white pattern, a color pattern or shading.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
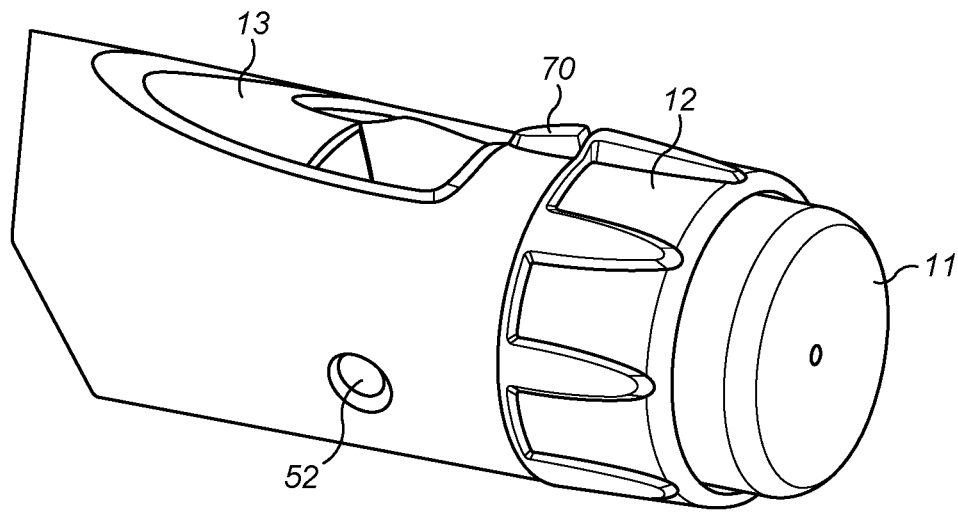

FIG. 1b is a close-up of the end of the injection device 1. This Fig. shows a locating rib 70 that is located between the viewing window 13 and the dosage knob 12.

Figure 2A:
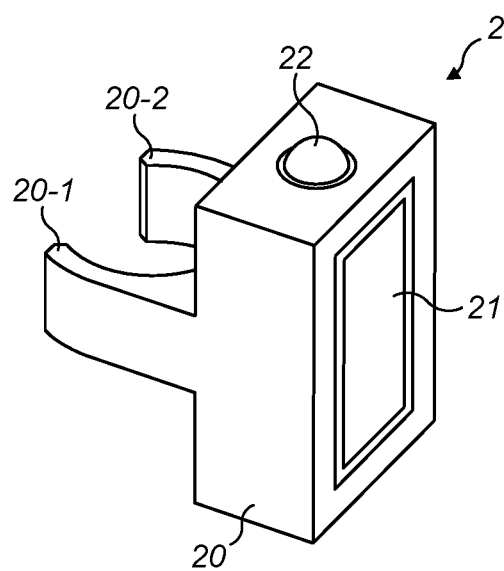
FIG. 2a: a schematic illustration of a supplementary device to be releasably attached to the drug delivery device of FIGS. 1a and 1b.

FIG. 2a is a schematic illustration of an embodiment of a supplementary device 2 (also referred to herein as an additional device 2, clip-on device 2 or sensor device 2) to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises at least one user input transducer, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
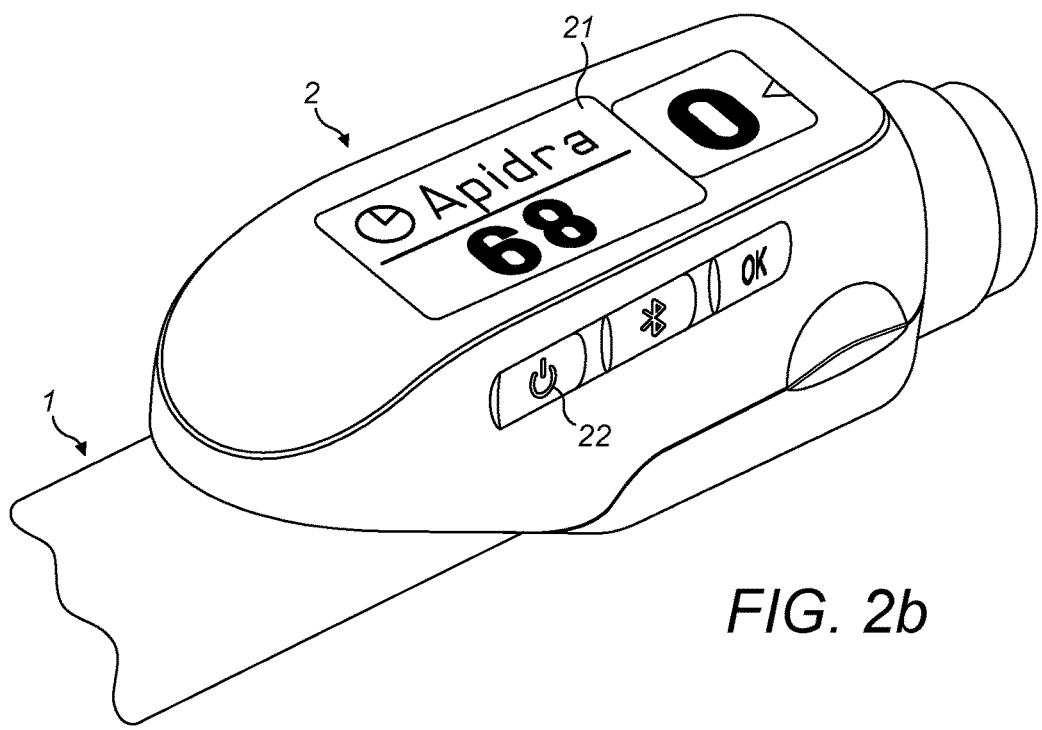
FIG. 2b: a perspective view of a supplementary device to be releasably attached to the drug delivery device.

FIG. 2b is a schematic illustration of a second embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
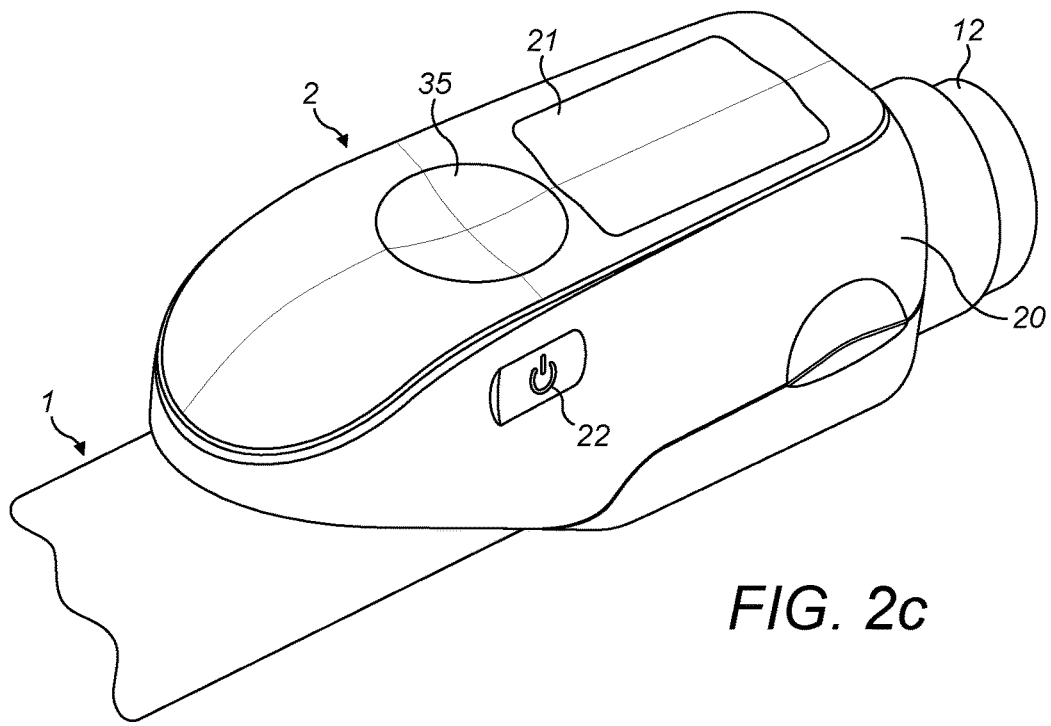
FIG. 2c: a perspective view of a supplementary device to be releasably attached to the drug delivery device of FIGS. 1a and 1b according to other aspects.

FIG. 2c is a schematic illustration of a third embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3:
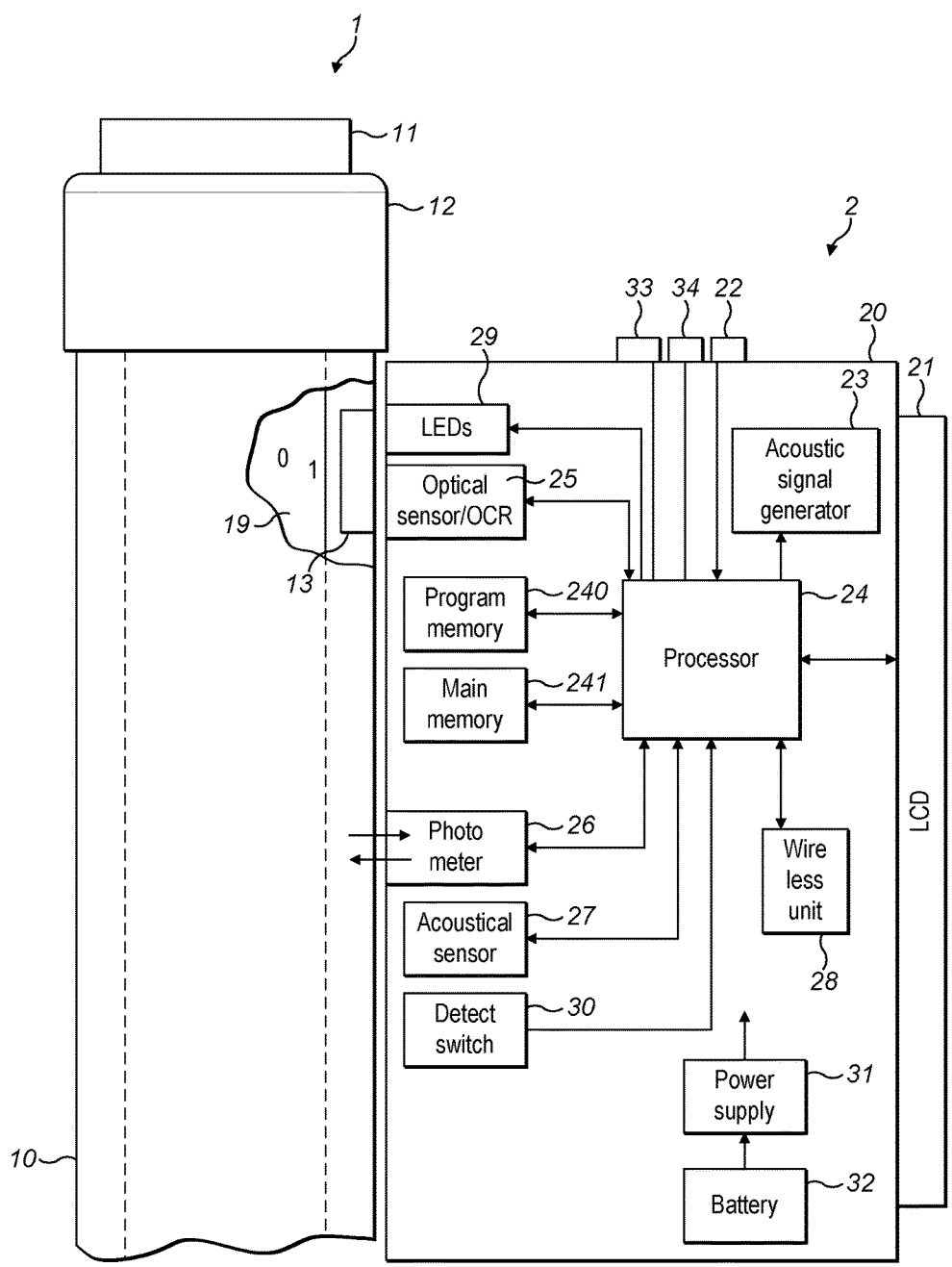
FIG. 3: a schematic view of a supplementary device attached to a drug delivery device showing components of the supplementary device.

FIG. 3 shows a schematic view of the supplementary device 2 of FIG. 2a in a state where it is attached to injection device 1 of FIG. 1.

With the housing 20 of supplementary device 2, a plurality of components are contained. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by way of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses. The magnification ratio (image size to object size ratio) may be smaller than 1. The magnification ratio may be in the range of 0.05 to 0.5. In one embodiment the magnification ratio may be 0.15.

Processor 24 further controls a photometer 26, that is configured to determine an optical property of the housing 10 of injection device 1, for example a color or a shading. The optical property may only be present in a specific portion of housing 10, for example a color or color coding of sleeve 19 or of an insulin container comprised within injection device 1, which color or color coding may for instance be visible through a further window in housing 10 (and/or in sleeve 19). Information on this color is then provided to processor 24, which may then determine the type of injection device 1 or the type of insulin contained in injection device 1 (e.g. SoloStar Lantus with purple color and SoloStar Apidra with blue color). Alternatively, a camera unit may be used instead of photometer 26, and an image of the housing, sleeve or insulin container may then be provided to processor 24 to determine the color of the housing, sleeve or insulin container by way of image processing. Further, one or more light sources may be provided to improve reading of photometer 26. The light source may provide light of a certain wavelength or spectrum to improve color detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 3 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 4:
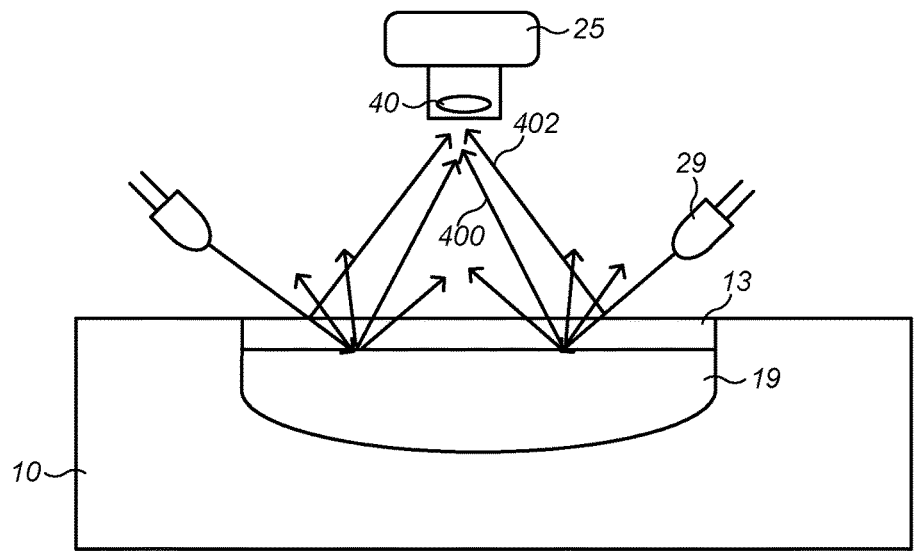
FIG. 4: a schematic view of a known configuration in which a supplementary device is attached to a drug delivery device.

FIG. 4 illustrates schematically a known arrangement of a supplementary device 2 attached to an injection device 1. Only parts of each of the devices are shown. The optical sensor 25 and LEDs 29 of the supplementary device 2 are shown. The supplementary device 2 also comprises a lens system 40 positioned in front of the optical sensor 25. A longitudinal cross-section through the pen body 10 showing the number sleeve 19 and dose window 13 represents the injection device 1.

The arrows 400, 402 in FIG. 4 illustrate light emitted from the LEDs 29 and reflections from both the number sleeve 19 and the dose window 13. Light emitted by the LEDs 29 which passes through the transparent dose window 3 and is incident on the number sleeve 19 is reflected back towards the optical sensor 25, allowing the optical sensor 25 to capture an image of the numbers printed on the number sleeve 19. This light path is illustrated by first arrows 400. The number sleeve 19 is moveable, such that different numbers are visible underneath the dose window 13, these numbers representing a dose of medicament programmed into the injection device 1. In some embodiments, the number sleeve 19 is a rotatable component and the numbers are printed on a circular or helical track on the surface of the number sleeve.

In general, the pen housing 10 is provided with an aperture and the dose window 13 is manufacture to fit securely within that aperture. Due to manufacturing requirements and cost considerations, the dose window 13 is not usually made of a highly non-reflective material or provided with a non-reflective coating. Therefore, some of the light incident on the dose window 13 will be reflected from the dose window 13, rather than passing through to be incident on the number sleeve 19. The second arrows 402 in FIG. 4 illustrate a light path in which reflections from the dose window 13 occur. These reflections lead to glare in the image captured by the optical sensor 25. As the LEDs 29 are point light sources, this glare generally takes the form of bright spots. The glare leads to areas of over-exposure and impacts the ability of the optical sensor 25 to capture a high quality image of the numbers printed on the number sleeve 19, which in turn affects the ability of the processor 24 to perform a successful optical character recognition process on the numbers. It can be particularly hard to avoid glare in the captured image because the dose window 13 is curved (as the pen body 10 is cylindrical) and so the light is incident on the dose window 13 over a range of angles.

Figure 5:
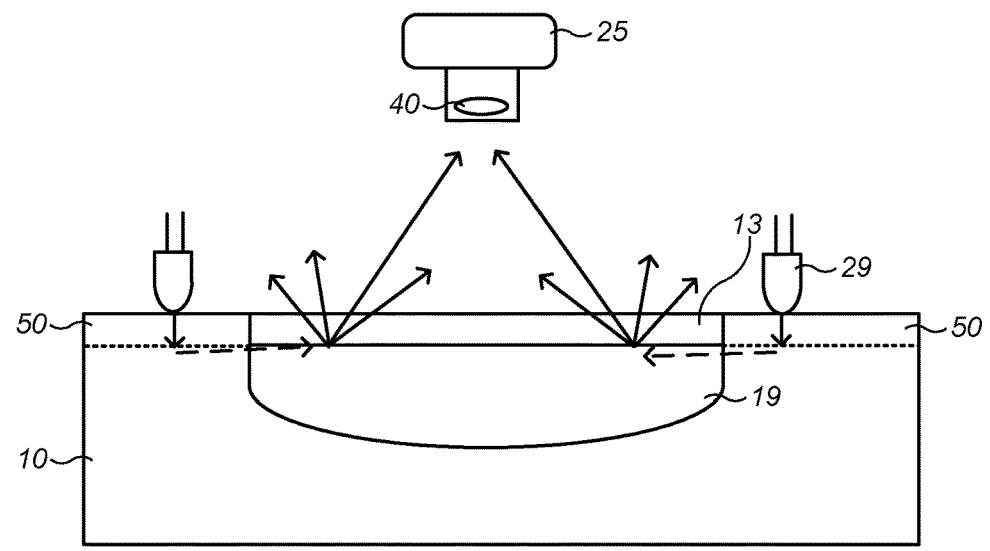
FIG. 5: a schematic view of a new configuration in which a supplementary device is attached to a modified drug delivery device.

Referring now to FIG. 5, a new arrangement of the injection device 1 and supplementary device 2 is shown. In this new arrangement, the pen housing 10 is provided with one or more regions 50, located adjacent to the dose window 13, which are themselves transparent to the light emitted by the LEDs 29. The transparent regions 50 are in optical communication with the dose window 13 so that light input into the transparent regions can enter the dose window 13.

In some embodiments, the transparent regions 50 are light guides made of a material that is optically transparent at visible wavelengths. The transparent regions 50 may also be transparent to UV and/or IR radiation. The transparent regions may be made of the same material as the dose window 13, or of a different material. The injection device 1 may be modified to accommodate the transparent regions 50. For example, the aperture in the pen housing 10 may be enlarged. Since light does not need to pass all the way through the transparent regions 50, the pen housing 10 may instead be provided with recesses, adjacent the aperture, in which the transparent regions 50 can be located. The light guides may comprise a disruptive structure which causes light entering the guide to be diffused. This disruptive structure may, for example, take the form of semi-circular indentations on the upper surface of the light guide. Thus a high percentage of the light entering the light guide's upper surface at an angle is reflected internally until it reaches the edge of the dose window 13. This effect may be enhanced by a further microstructure on the lower surface of the light guide which causes light to be reflected in the direction of the dose window 13. Although there may be some reflection at the boundary between the light guide and the dose window 13, sufficient light enters the dose window 13 to illuminate the number sleeve 19. Using diffused light further reduces the possibility of unwanted reflections impacting the ability of the optical sensor 25 to capture a high quality image.

The light guides may be rectangular in cross section and have a curved plate like structure. Some internal surfaces of the light guides may be provided with a reflective coating to increase the amount of light reflected towards the dose window 13. For example, the curved end furthest from the light guide/dose window interface may have a reflective coating.

The positions of the LEDs 29 in the supplementary device 2 may be modified compared with the known arrangement shown in FIG. 4. For example, instead of shining at an angle onto the dose window 13, the LEDs 29 may be located directly above the light guides and orientated perpendicular to the light guide surface. This may require that the LEDs 29 be supported in a different location on the underside of the supplementary device 2 such that they are further away from the dose window 13. Alternatively, the position of the LEDs 29 may be the same and it may be only the orientation of the LEDs 29 which is changed. In some other embodiments, the LEDs 29 are located further away from the edges of the dose window 13 than in the known configuration, but still some distance away from the surface of the light guides. This may ensure that light from the LEDs 29 is not directly incident on the dose window 13, or is incident at a very shallow angle which does not cause reflection to be seen by the optical sensor 25. The LEDs 29 may also be orientated at an angle to the light guides such that a majority of light enters the light guides at an angle and undergoes internal reflection before being out-coupled into the dose window 13. In some embodiments a screen may be provided to block light from the LEDs 29 shining directly onto the dose window 13. This screen may be on the underside of the supplementary device 2 or may comprise protrusions on the pen housing 10.

In some other embodiments, the LEDs 29 may emit UV light. Part or all of the number sleeve 19 may be UV reflective. For example, the numbers printed on the number sleeve 19 may be printed in a UV reflective ink. Therefore, only the numbers will appear to be illuminated when the LEDs 29 are activated. This may improve the visibility of the numbers low light conditions.

In some embodiments the transparent regions 50 may comprise a continuous extension of the dose window 13, such that there is no interface through which light must pass. The transparent regions 50 may be of the same thickness as the dose window 13, or of a different thickness.

In some other embodiments, the transparent regions 50 may comprise apertures in the pen housing 10 i.e. the regions are comprised of empty space. The LEDs 29 may be positioned such that light is directly incident on the number sleeve 19 without having to pass through the dose window 13 and/or such that light is directly incident only on the curved end surfaces of the dose window 13. The position of the LEDs 29 may need to be modified such that they are very close to the injection device 1 when the supplementary device 2 is attached, or such that they enter the apertures in the pen housing 10, in order to achieve the right angle of illumination.

One or more transparent regions 50 may be provided. For example, the supplementary device 2 may have two LEDs 29 located longitudinally before and after the dose window 13. Two corresponding transparent regions 50 on opposite sides of the dose window 13 are provided, as shown in FIG. 5. Alternatively, the supplementary device 2 may have two LEDs 29 located on each side of the dose window 13 (four LEDs 29 in total). The two transparent regions 50 on either side of the window may be enlarged to allow light from all four LEDs 29 to enter. The dose window 13 is in general a curved plate having two pairs of parallel edges. The transparent regions 50 may be located adjacent one or both of these pairs of edges. The transparent regions 50 may completely surround the dose window 13 on all sides. In some other embodiments, the dose window 13 may be round, oval, oblong or an irregular shape and the transparent regions 50 may surround a part of or all of the outer edge of the dose window 13. By providing transparent regions 50 on multiples sides of the dose window 13, a more even illumination of the number sleeve 19 is achieved.

The invention claimed is:

1. A drug delivery device comprising:
   a housing;
   a moveable number sleeve disposed within the housing and having numbers printed thereon; and
   a transparent window that is separate from the housing, the transparent window occupying an aperture of the housing and covering the number sleeve such that the number sleeve is visible through the transparent window,
   wherein at least one region of the housing located adjacent the transparent window comprises one or more light guides configured to receive input light from a source external to the drug delivery device and to output the light into the transparent window so as to cause illumination of the number sleeve.

2. The drug delivery device according to claim 1, wherein at least one internal surface of the one or more light guides is reflective.

3. The drug delivery device according to claim 1, wherein the housing comprises two regions of transparent material located in respective recesses of the housing adjacent to opposite sides of the transparent window.

4. The drug delivery device according to claim 1, wherein the transparent window and the at least one region of the housing located adjacent the transparent window are made of different materials.

5. The drug delivery device according to claim 1, wherein the housing comprises one or more recesses located adjacent the aperture of the housing.

6. The drug delivery device according to claim 5, wherein the at least one region of the housing located adjacent the transparent window is arranged in the one or more recesses of the housing.

7. The drug delivery device according to claim 1, wherein the one or more light guides comprise semi-circular indentations on an upper surface of the one or more light guides.

8. A system comprising a drug delivery device and a supplementary device, the drug delivery device comprising:
   a housing;
   a moveable number sleeve disposed within the housing and having numbers printed thereon; and
   a transparent window that is separate from the housing, the transparent window occupying an aperture of the housing and covering the number sleeve such that the number sleeve is visible through the transparent window, and;
   the supplementary device comprising:
      an imaging arrangement configured to capture an image of the number sleeve of the drug delivery device, the number sleeve disposed beneath the transparent window; and
      one or more illumination sources configured to illuminate the number sleeve indirectly by being positioned such that when the supplementary device is attached to the drug delivery device, light from the one or more illumination sources is incident on at least one region of the housing located adjacent the transparent window,
   wherein the at least one region of the housing located adjacent the transparent window comprises one or more light guides configured to receive input light from the one or more illumination sources of the supplementary device when the supplementary device is attached to the drug delivery device and to output the light into the transparent window so as to cause illumination of the number sleeve.

9. A method to measure information related to a drug delivery device comprising:
   configuring a supplementary device, containing an imaging arrangement, to be attached to a housing of a drug delivery device, the drug delivery device comprising an optically transparent window that is separate from the housing and occupies an aperture of the housing and covers a movable number sleeve disposed within the housing such that the number sleeve is visible through the transparent window, the number sleeve having numbers printed thereon, wherein at least one region of the housing located adjacent the transparent window comprises one or more light guides configured to receive input light from a source external to the drug delivery device and to output the light into the transparent window so as to cause illumination of the number sleeve,
   collecting optical data from preparation and use of the drug delivery device via the supplementary device, and
   processing and displaying the optical data via a display unit on the supplementary device.

10. The method of claim 9, wherein the supplementary device is attached to the housing of the drug delivery device using a releasable mating unit.

11. The method of claim 9, further comprising attaching the supplementary device to the housing of the drug delivery device by aligning the imaging arrangement of the supplementary device to the transparent window of the drug delivery device, such that the imaging arrangement can view at least one of the numbers printed on the number sleeve beneath the transparent window.

12. The method of claim 9, wherein the step of collecting optical data is executed using an optical sensor, a photometer, and the source external to the drug delivery device.

13. A system comprising:
a drug delivery device comprising:
   a housing;
   a moveable number sleeve disposed within the housing and having numbers printed thereon; and
   a transparent window that is separate from the housing, the transparent window occupying an aperture of the housing and covering the number sleeve such that the number sleeve is visible through the transparent window, and
a supplementary device for attachment to the drug delivery device, the supplementary device comprising:
   an imaging arrangement configured to capture an image of the moveable number sleeve of the drug delivery device, the number sleeve disposed beneath the transparent window; and
   one or more illumination sources configured to illuminate the number sleeve indirectly by being positioned such that when the supplementary device is attached to the drug delivery device light from the one or more illumination sources is incident on at least one region of the housing located adjacent the transparent window,
wherein the at least one region of the housing located adjacent the transparent window comprises one or more light guides configured to receive input light from the one or more illumination sources of the supplementary device when the supplementary device is attached to the drug delivery device and to output the light into the transparent window so as to cause illumination of the number sleeve.

* * * * *